United States Patent
Lee et al.

(10) Patent No.: US 6,806,025 B2
(45) Date of Patent: Oct. 19, 2004

(54) PHOTORESIST MONOMERS, POLYMERS THEREOF AND PHOTORESIST COMPOSITONS CONTAINING THE SAME

(75) Inventors: Geun Su Lee, Kyoungki-do (KR); Jae Chang Jung, Kyoungki-do (KR); Ki Soo Shin, Kyoungki-do (KR)

(73) Assignee: Hynix Semiconductor Inc., Kyoungki-di (KR)

( * ) Notice: Subject to any disclaimer, the term of this patent is extended or adjusted under 35 U.S.C. 154(b) by 319 days.

(21) Appl. No.: 10/079,348

(22) Filed: Feb. 20, 2002

(65) Prior Publication Data

US 2003/0003379 A1 Jan. 2, 2003

(30) Foreign Application Priority Data

Jun. 19, 2001 (KR) .......................... 2001-34603

(51) Int. Cl.[7] .......................... G03F 7/004; G08F 36/00; G08F 126/06
(52) U.S. Cl. ................. 430/270.1; 430/326; 526/219.6; 526/232.1; 526/242; 526/281; 526/258; 526/319
(58) Field of Search .............................. 430/270.1, 326; 526/242, 281, 319, 219.6, 258, 232.1

(56) References Cited

PUBLICATIONS

CA 118:102781, Seehof, et al. J.Mol.Catalyst, 1992, 76(1–3),53–63.*

\* cited by examiner

Primary Examiner—Rosemary Ashton
(74) Attorney, Agent, or Firm—Marshall, Gerstein & Borun LLP (57) ABSTRACT

Photoresist monomers of following Formula 1, photoresist polymers thereof, and photoresist compositions containing the same. The photoresist composition has excellent etching resistance, heat resistance and adhesiveness to a wafer, and is developable in aqueous tetramethylammonium hydroxide (TMAH) solution. In addition, the photoresist composition has low light absorbance at 157 nm wavelength, and thus is suitable for a photolithography process using ultraviolet light sources such as VUV (157 nm) in fabricating a minute circuit for a high integration semiconductor device.

Formula 1

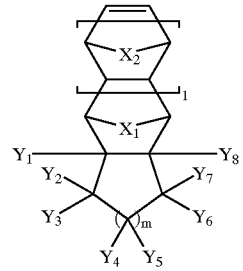

wherein, $X_1$, $X_2$, $Y_1$, $Y_2$, $Y_3$, $Y_4$, $Y_5$, $Y_6$, $Y_7$, $Y_8$, l and m are as defined in the specification of the invention.

23 Claims, 3 Drawing Sheets

PHOTORESIST MONOMERS, POLYMERS THEREOF AND PHOTORESIST COMPOSITONS CONTAINING THE SAME

BACKGROUND

1. Technical Field

Photoresist monomers, polymers thereof and photoresist compositions containing the same are disclosed. In particular, photoresist monomers suitable for a photolithography process using DUV (deep ultraviolet) light sources, particularly VUV (vacuum ultraviolet: 157 nm) in fabricating a minute circuit for a high integration semiconductor device, photoresist polymers thereof, photoresist compositions containing the same, and preparation processes are also disclosed.

2. Description of the Related Art

In general, a useful photoresist for ArF and VUV has a variety of desired characteristics, such as low light absorbance at the wavelength of 193 nm and 157 nm, excellent etching resistance, and excellent adhesiveness to a wafer. In addition, a photoresist should be easily developable in a commercially readily available developing solution, such as 2.38 wt % and 2.6 wt % aqueous tetramethylammonium hydroxide (TMAH) solution.

Recently, much research has been conducted on resins having a high transparency at the wavelength of 248 nm and 193 nm and dry etching resistance similar to novolac resin. However, most of the photoresists are not suitable for VUV due to their poor transmittance at 157 nm wavelength.

Photoresists containing fluorine have good transmittance at these wavelengths. Unfortunately, most photoresists containing fluorine with a polyethylene, polystyrene or polyacrylate polymer backbone have weak etching resistance, low solubility in an aqueous TMAH solution and poor adhesiveness to the silicon wafer. In addition, these photoresists are difficult to mass-produce and are expensive.

On the other hand, photoresists containing fluorine with alicyclic polymer or maleicanhydride-norbonene polymer backbone have good adhesiveness to the silicon wafer, low light absorbance at the wavelength of 157 nm and excellent etching resistance compared to photoresists with polyacrylate backbone.

SUMMARY OF THE DISCLOSURE

Accordingly, novel photoresist monomers, polymers thereof and photoresist compositions containing the same that can be used for a light sources such as ArF (193 nm) and VUV (157 nm) are disclosed.

A process for forming a photoresist pattern using the photoresist compositions described above and a semiconductor element produced by using the process described above are also disclosed.

DETAILED DESCRIPTION OF THE PRESENTLY PREFERRED EMBODIMENTS

First, a photoresist monomer is disclosed that is represented by following Formula 1:

Formula 1 wherein, $X_1$ and $X_2$ individually are selected from the group consisting of $C_1$–$C_{10}$)alkylene, O and S;

$Y_1$, $Y_2$, $Y_3$, $Y_4$, $Y_5$, $Y_6$, $Y_7$ and $Y_8$ individually are selected from the group consisting of halogen and an alkyl partially or wholly substituted with halogen, more preferably F, Cl, Br, I or $CF_3$; and l and m are individually integers from 0 to 3.

Some of preferred photoresist monomers are disclosed, but are not limited to, as following Formulas 1a to 1d:

Formula 1a

Formula 1b

Formula 1c

; and

Formula 1d

The compound of above Formula 1, can be obtained by reacting cycloalken of following Formula 2 and cycloalken substituted with halogen or $CF_3$ of following Formula 3.

Formula 2

Formula 3 wherein, $X_1$ is selected from the group consisting of $(C_1-C_{10})$alkylene, O and S;

$Y_1$, $Y_2$, $Y_3$, $Y_4$, $Y_5$, $Y_6$, $Y_7$ and $Y_8$ individually are selected from the group consisting of halogen and an alkyl partially or wholly substituted with halogen, more preferably F, Cl, Br, I or $CF_3$; and m is integer from 0 to 3.

In addition, a repeating unit is represented by following Formula 4 comprising the compound of Formula 1 as a comonomer and photoresist polymer comprising the repeating unit of Formula 4.

Formula 4 wherein, $R_1$, $R_2$ and $R_3$ individually are selected from the group consisting of H, halogen, $(C_1-C_{20})$ alkyl, $(C_1-C_{20})$ alkyl with halogen substituent(s), $(C_1-C_{20})$ alkyl containing an ether group (—O—), and $(C_1-C_{20})$ alkyl with halogen substituent(s) and containing an ether group;

$R_4$ is an acid labile protecting group;

$X_1$ and $X_2$ individually are selected from the group consisting of $(C_1-C_{10})$alkylene, O and S;

$Y_1$, $Y_2$, $Y_3$, $Y_4$, $Y_5$, $Y_6$, $Y_7$ and $Y_8$ individually are selected from the group consisting of halogen and alkyl partially or wholly substituted with halogen;

Z is O or S;

l and m are individually integers from 0 to 3;

n is 0 or 1; and a:b:c falls within the ranges 0–60 mol %:5–80 mol %:0–90 mol %.

More preferably, above $R_1$, $R_2$ and $R_3$ individually are selected from the group consisting of H, F, $(C_1-C_{20})$ alkyl, $(C_1-C_{20})$ perfluoroalkyl, $(C_1-C_{20})$ alkyl containing an ether group, $(C_1-C_{20})$ perfluoroalkyl containing an ether group, $(C_1-C_{20})$ alkyl partially substituted with F, and $(C_1-C_{20})$ alkyl partially substituted with F and containing an ether group, and, above $Y_1$, $Y_2$, $Y_3$, $Y_4$, $Y_5$, $Y_6$, $Y_7$ and $Y_8$ individually are selected from the group consisting of F, Cl, Br, I and $CF_3$.

And the acid labile protecting group can be any of known protecting groups which prevent the compound from dissolving in an alkaline developing solution. However, under the presence of acid, the acid labile group is substituted with acid, thereby making the compound soluble to the alkaline solution. Some of conventional acid labile protecting groups are disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0789 278 (Aug. 13, 1997), U.S. Pat. No. 6,132,926 (Oct. 17, 2000), U.S. Pat. No. 6,143,463 (Nov. 7, 2000), U.S. Pat. No. 6,150,069 (Nov 21, 2000), U.S. Pat. No. 6,180,316 B1 (Jan. 30, 2001), U.S. Pat. No. 6,225,020 B1 (May 1, 2001), U.S. Pat. No. 6,235,448 B1 (May 22, 2001) and U.S. Pat. No. 6,235,447 B1 (May 22, 2001). Acid labile protecting groups of the present invention are preferably selected from the group consisting of tert-butyl, tetrahydropyran-2-yl, 2-methyl tetrahydropyran-2-yl, tetrahydrofuran-2-yl, 2-methyl tetrahydrofuran-2-yl, 1-methoxypropyl, 1-methoxy-1-methylethyl, 1-ethoxypropyl, 1-ethoxy-1-methylethyl, 1-methoxyethyl, 1-ethoxyethyl, tert-butoxyethyl, 1-isobutoxyethyl and 2-acetylmenth-1-yl.

Some of preferred repeating unit of above Formula 4 are disclosed, but are not limited to, as following Formulas 4a to 4d:

Formula 4a

;

Formula 4b

;

Formula 4c

; and

-continued

Formula 4d wherein, the ratio a:b:c falls within the ranges 0–60 mol %:5–80 mol %:0–90 mol %.

The process for preparing of a photoresist polymer comprising the repeating unit of Formula 4 will now be explained in more detail.

The disclosed repeating unit of above Formula 4 can be prepared by radical-polymerization the compound of above Formula 1 and optionally maleimide derivative of following Formula 5 or acrylate derivative of following Formula 6. The process comprises:

(a) admixing (i) a compound of Formula 1 and optionally (ii) the compound of Formula 5 or the compound of Formula 6; and (b) adding a polymerization initiator into the resultant of step (a) to obtain a repeating unit of Formula 4.

Formula 5

Formula 6 wherein, $R_1$, $R_2$ and $R_3$ individually are selected from the group consisting of H, halogen, ($C_1$–$C_{20}$) alkyl, ($C_1$–$C_{20}$) alkyl with halogen substituent(s), ($C_1$–$C_{20}$) alkyl containing an ether group, and ($C_1$–$C_{10}$) alkyl with halogen substituent(s) and containing an ether group;

$R_4$ is an acid labile protecting group;

Z is O or S; and n is 0 or 1.

More preferably, above $R_1$, $R_2$ and $R_3$ individually are selected from the group consisting of H, F, ($C_1$–$C_{20}$) alkyl, ($C_1$–$C_{20}$) perfluoroalkyl, ($C_1$–$C_{20}$) alkyl containing an ether group, ($C_1$–$C_{20}$) perfluoroalkyl containing an ether group, ($C_1$–$C_{20}$) alkyl partially substituted with F, and ($C_1$–$C_{20}$) alkyl partially substituted with F and containing an ether group.

And the acid labile protecting group is same as mentioned above.

In the above process, radical polymerization is carried out by bulk polymerization or solution polymerization.

In case it is carried out by solution polymerization, the organic solvents suitable for polymerization can be cyclohexanone, cyclopentanone, tetrahydrofuran, dimethylformamide, dimethylsulfoxide, dioxane, methylethylketone, benzene, toluene, xylene or mixtures thereof.

The polymerization initiators can be any conventional one, preferably a radical polymerization initiators such as 2,2'-azobisisobutyronitrile(AIBN), benzoyl peroxide, acetyl peroxide, lauryl peroxide, tert-butyl peracetate or di-tert-butyl peroxide.

On the other hand, the repeating unit can be prepared by using metal catalyst as disclosed in WO 96/37526 (Nov. 28, 1996).

More preferably, after polymerization, the repeating unit is subject to crystallization and/or purification by using diethyl ether, petroleum ether, alcohol, water or mixtures thereof.

A photoresist polymer comprises the above repeating unit in the main chain and further comprises other comonomers or additives as occasion demands.

In addition, a photoresist composition comprises (i) a photoresist polymer described above; (ii) a photoacid generator; and (iii) an organic solvent.

Any of conventional photoacid generator, which is able to generate acids when it is exposed to light, can be used. Some of conventional photoacid generator are disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0789 278 (Aug. 13, 1997) and U.S. Pat. No. 6,132,926 (Oct. 17, 2000), U.S. Pat. No. 6,143,463 (Nov. 7, 2000), U.S. Pat. No. 6,150,069 (Nov. 21, 2000), U.S. Pat. No. 6,180,316 B1 (Jan. 30, 2001), U.S. Pat. No. 6,225,020 B1 (May 1, 2001), U.S. Pat. No. 6,235,448 B1 (May 22, 2001) and U.S. Pat. No. 6,235,447 B1 (May 22, 2001).

Preferred photoacid generators have relatively low light absorbance in the wavelength of 157 nm and 193 nm. More preferred photoacid generator is phthalimidotrifluoromethane sulfonate, dinitrobenzyltosylate, n-decyl disulfone, naphthylimido trifluoromethane sulfonate or mixtures thereof.

The photoacid generator can further comprise a compound selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, triphenylsulfonium hexafluoroarsenate, triphenylsulfonium hexafluoroantimonate, triphenylsulfonium triflate, dibutylnaphthylsulfonium triflate and mixtures thereof.

Typically, the amount of photoacid generator is from about 0.05 to about 10% by weight of the photoresist polymer employed. It has been found that when the photoacid generator is used in the amount less than about 0.05%, it lowers photosensitivity of the photoresist composition, and when the photoacid generator is used in the amount greater than about 10%, it results in a poor pattern formation due to its high absorption.

On the other hand, any of conventional organic solvent can be employed for this invention and some of the conventional one are also disclosed in the documents described above. Preferred organic solvents for photoresist composition is methyl 3-methoxypropionate, ethyl 3-ethoxypropionate, propylene glycol methyl ether acetate, cyclohexanone, 2-heptanone, ethyl lactate or mixture thereof.

The amount of organic solvent ranges from about 500 to about 2000% by weight of the photoresist polymer to coat the photoresist in a wanted thickness. It has been found that when the organic solvent is used in the amount of about 1000 wt %, a thickness of the photoresist is about 0.25 μm.

A process for forming a photoresist pattern comprises:

(a) coating the photoresist composition described above on a substrate to form a photoresist film;

(b) exposing the photoresist film to light; and (c) developing the exposed photoresist film to obtain a photoresist pattern.

The process for forming the photoresist pattern can further include a soft baking which is preformed before the step (b) and/or a post baking step which is preformed after the step (b). Preferably, the soft and post baking steps are performed at temperature in the range of from about 70 to about 200° C.

Exemplary light sources which are useful for forming the photoresist pattern include not only VUV but also ArF, KrF, E-beam, EUV or ion beam. Preferably, the irradiation energy in the step (b) is in the range of from about 1 mJ/cm$^2$ to about 100 mJ/cm$^2$.

On the other hand, the step (c) can be performed in alkaline developing solution which is preferably TMAH aqueous solution with a concentration ranging from about 0.01 to about 5 wt %.

In addition, a semiconductor device can be manufactured using the photoresist compositions described above.

The disclosed monomers, polymers and photoresist compositions will now be described in more details by referring to examples below, which are not intended to be limiting.

I. Preparation of Photoresist Monomers

EXAMPLE 1

Synthesis of Compound of Formula 1a

Cyclopentadiene(1 mole) and 1,2,2,3,3,4,4,5-octafluorocyclopentene(1 mole) were stirred for about 1 hour at about −10° C. and then the temperature was slowly raised to reach room temperature. At the same temperature, the reaction was proceeded for about 10 hours, thereby obtaining the following Formula 1a (yield 98%).

Formula 1a

EXAMPLE 2

Synthesis of Compound of Formula 1b

Furan(1 mole) and 1,2,2,3,3,4,4,5-octafluorocyclopentene(1 mole) were stirred for about 1 hour at about −10° C. and then the temperature was slowly raised to reach room temperature. At the same temperature, the reaction was proceeded for about 10 hours, thereby obtaining the following Formula 1b (yield 98%).

Formula 1b

EXAMPLE 3

Synthesis of Compound of Formula 1c

Cyclohexadiene(1 mole) and 1,2,2,3,3,4,4,5-octafluorocyclopentene(1 mole) were stirred for about 1 hour at about −10° C. and then the temperature was slowly raised to reach room temperature. At the same temperature, the reaction was proceeded for about 10 hours, thereby obtaining the following Formula 1c (yield 98%).

Formula 1c

EXAMPLE 4

Synthesis of Compound of Formula 1d

Thiopene(1 mole) and 1,2,2,3,3,4,4,5-octafluorocyclopentene(1 mole) were stirred for about 1 hour at about −10° C. and then the temperature was slowly raised to reach room temperature. At the same temperature, the reaction was proceeded for about 10 hours, thereby obtaining the following Formula 1d (yield 98%).

Formula 1d

II. Preparation of Photoresist Polymers

EXAMPLE 5

Synthesis of Compound of Formula 4a

To 10 mL of tetrahydrofuran was added ethylmaleimide (0.01 mole), the compound of Formula 1a obtained from Example 1(0.01 mole), tert-butyl-2-(trifluoromethyl)-acrylate(0.02 mole) and AIBN(0.4 g), and the resulting solution was reacted at about 65° C. for about 10 hours. Thereafter, a polymer was precipitated and filtered in diethyl ether solution, thereby obtaining the following Formula 4a (yield: 51%).

Formula 4a

EXAMPLE 6

Synthesis of Compound of Formula 4b

To 10 mL of tetrahydrofuran was added ethylmaleimide (0.01 mole), the compound of Formula 1b obtained from Example 2(0.01 mole), tert-butyl-2-(trifluoromethyl)-acrylate(0.02 mole) and AIBN(0.4 g), and the resulting solution was reacted at about 65° C. for about 10 hours. Thereafter, a polymer was precipitated and filtered in diethyl ether solution, thereby obtaining the following Formula 4b (yield: 51%).

Formula 4b

EXAMPLE 7

Synthesis of Compound of Formula 4c

To 10 mL of tetrahydrofuran was added ethylmaleimide (0.01 mole), the compound of Formula 1c obtained from Example 3(0.01 mole), tert-butyl-2-(trifluoromethyl)-acrylate(0.02 mole) and AIBN(0.4 g), and the resulting solution was reacted at about 65° C. for about 10 hours. Thereafter, a polymer was precipitated and filtered in diethyl ether solution, thereby obtaining the following Formula 4a (yield: 51%).

Formula 4c

EXAMPLE 8

Synthesis of Compound of Formula 4d

To 10 mL of tetrahydrofuran was added ethylmaleimide (0.01 mole), the compound of Formula 1d obtained from Example 4(0.01 mole), tert-butyl-2-(trifluoromethyl)-acrylate(0.02 mole) and AIBN(0.4 g), and the resulting solution was reacted at about 65° C. for about 10 hours. Thereafter, a polymer was precipitated and filtered in diethyl ether solution, thereby obtaining the following Formula 4d (yield: 51%).

Formula 4d

III. Preparation of Photoresist Compositions and Formation of Patterns

EXAMPLE 9

Preparation of Photoresist Compositions and Formation of Patterns(1)

To 20 g of propylene glycol methyl ether acetate (PGMEA) was added 2 g of the compound of Formula 4a obtained from Example 5, 0.024 g of phthalimidotrifluoromethane sulfonate, and 0.06 g of triphenylsulfonium triflate. The polymer was precipitated and filtered in 0.20 $\mu$m filter to obtain a photoresist composition.

Figure 1:
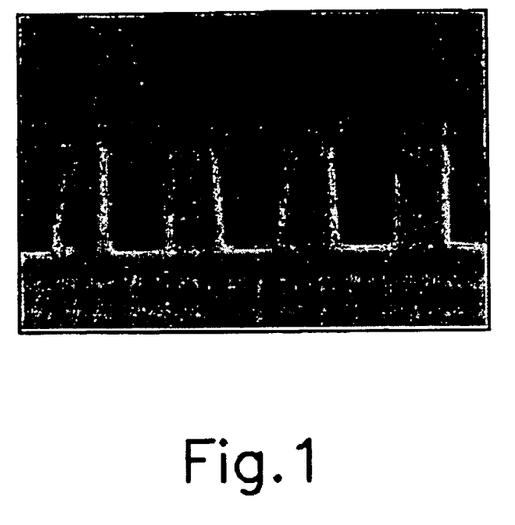
FIG. 1 is a photograph of a photoresist pattern obtained from Example 9.

The photoresist composition thus prepared was spin-coated on silicon wafer to form a photoresist film, and soft-baked at about 130° C. for about 90 seconds. After baking, the photoresist was exposed to light using a KrF laser exposer, and then post-baked at about 130° C. for about 90 seconds. When the post-baking was completed, it was developed in 2.38 wt % aqueous TMAH solution for 40 seconds, to obtain 0.13 $\mu$m L/S pattern (see FIG. 1).

EXAMPLE 10

Preparation of Photoresist Compositions and Formation of Patterns(2)

To 20 g of propylene glycol methyl ether acetate (PGMEA) was added 2 g of the compound of Formula 4b obtained from Example 6, 0.024 g of phthalimidotrifluoromethane sulfonate, and 0.06 g of triphenylsulfonium triflate. The polymer was precipitated and filtered in 0.20 $\mu$m filter to obtain a photoresist composition.

Figure 2:
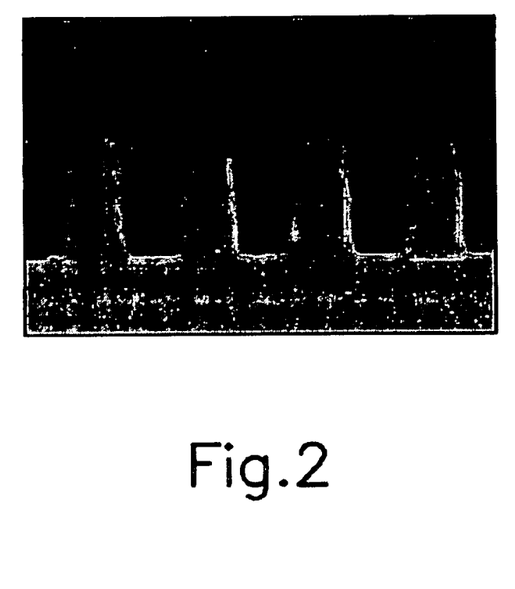
FIG. 2 is a photograph of a photoresist pattern obtained from Example 10.

The photoresist composition thus prepared was spin-coated on silicon wafer to form a photoresist film, and soft-baked at about 130° C. for about 90 seconds. After baking, the photoresist was exposed to light using a KrF laser exposer, and then post-baked at about 130° C. for about 90 seconds. When the post-baking was completed, it was developed in 2.38 wt % aqueous TMAH solution for 40 seconds, to obtain 0.13 $\mu$m L/S pattern (see FIG. 2).

EXAMPLE 11

Preparation of Photoresist Compositions and Formation of Patterns(3)

To 20 g of propylene glycol methyl ether acetate (PGMEA) was added 2 g of the compound of Formula 4c obtained from Example 7, 0.024 g of phthalimidotrifluoromethane sulfonate, and 0.06 g of triphenylsulfonium triflate. The polymer was precipitated and filtered in 0.20 μm filter to obtain a photoresist composition.

Figure 3:
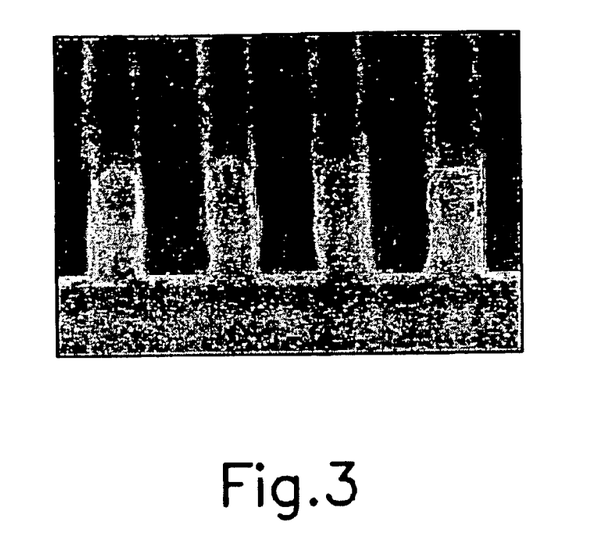
FIG. 3 is a photograph of a photoresist pattern obtained from Example 11.

The photoresist composition thus prepared was spin-coated on silicon wafer to form a photoresist film, and soft-baked at about 130° C. for about 90 seconds. After baking, the photoresist was exposed to light using a KrF laser exposer, and then post-baked at about 130° C. for about 90 seconds. When the post-baking was completed, it was developed in 2.38 wt % aqueous TMAH solution for 40 seconds, to obtain 0.13 μm L/S pattern (see FIG. 3).

EXAMPLE 12

Preparation of Photoresist Compositions and Formation of Patterns(4)

To 20 g of propylene glycol methyl ether acetate (PGMEA) was added 2 g of the compound of Formula 4d obtained from Example 8, 0.024 g of phthalimidotrifluoromethane sulfonate, and 0.06 g of triphenylsulfonium triflate. The polymer was precipitated and filtered in 0.20 μm filter to obtain a photoresist composition.

Figure 4:
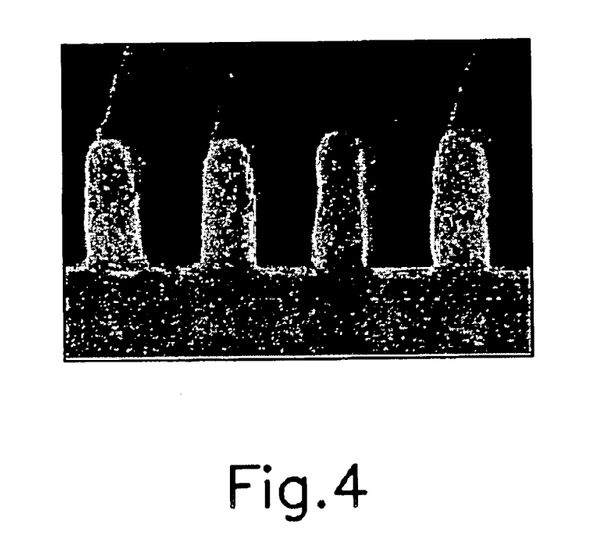
FIG. 4 is a photograph of a photoresist pattern obtained from Example 12.

The photoresist composition thus prepared was spin-coated on silicon wafer to form a photoresist film, and soft-baked at about 130° C. for about 90 seconds. After baking, the photoresist was exposed to light using a KrF laser exposer, and then post-baked at about 130° C. for about 90 seconds. When the post-baking was completed, it was developed in 2.38 wt % aqueous TMAH solution for 40 seconds, to obtain 0.13 μm L/S pattern (see FIG. 4).

Experimental Example

Investigation of a Light Absorbance at 157 nm Wavelength

Figure 5:
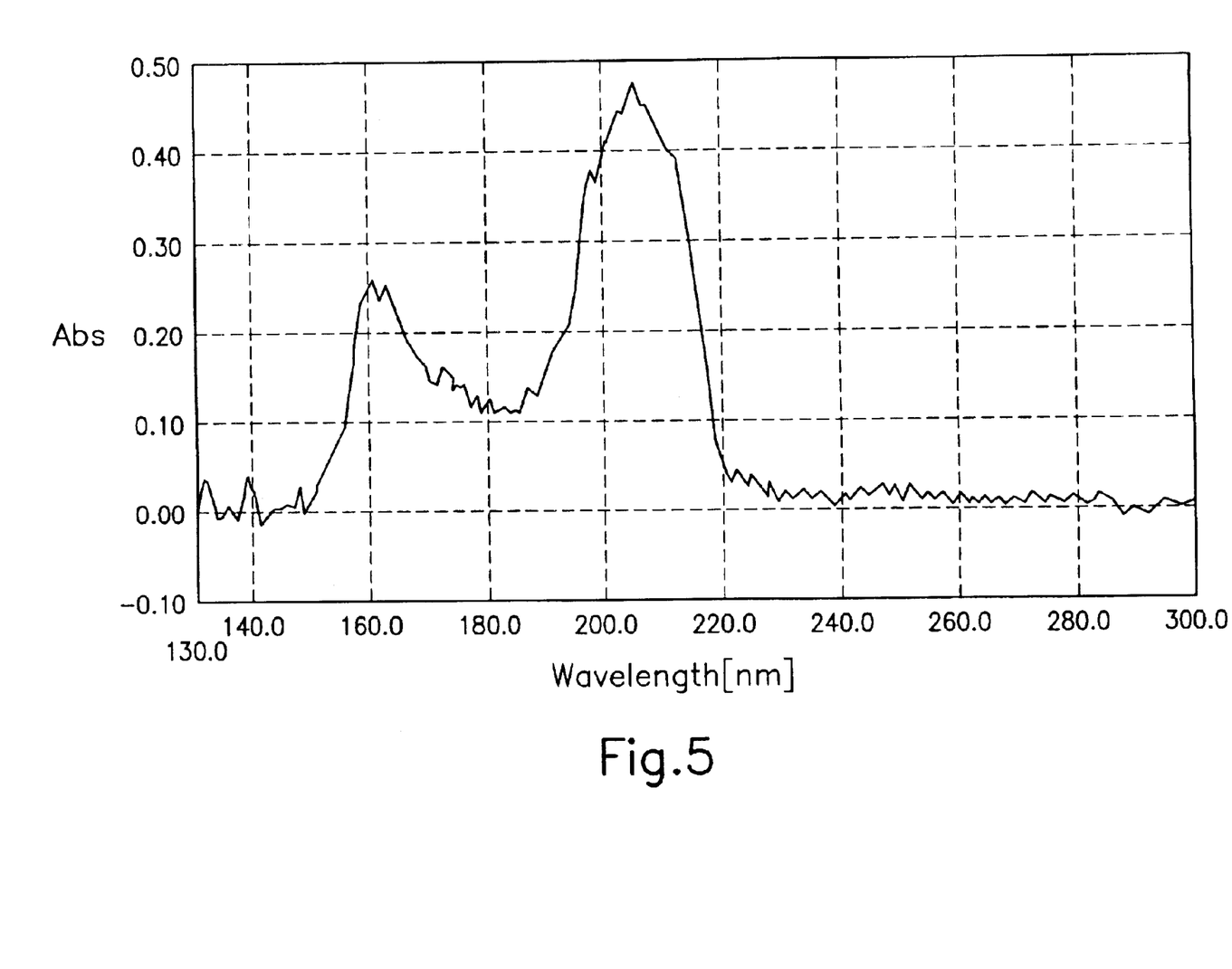
FIG. 5 is a VUV spectrum for a photoresist composition obtained from Example 9.

A light absorbance of photoresist composition obtained from Example 9 coated in a thickness of about 2500 Å was shown by VUV spectrum of FIG. 5. According to FIG. 5, the light absorbance of photoresist composition obtained from Example 9 at 157 nm wavelength is 0.22 which is only below half of the light absorbance of usual KrF or ArF photoresist. Therefore, the conventional photoresist composition should be coated below a thickness of 700 Å in order to satisfy a light transmittance when it used in the photolithography employing the light of 157 nm. While a photoresist pattern can be formed successfully using a photoresist composition of this present invention though it coated over a thickness of about 1000 Å because of excellent transmittance at 157 nm wavelength. In this way, the present invention can obtain a more increased etching resistance because photoresist film can be formed sufficient thickness.

The above Experimental Example implies that photoresist composition comprising photoresist polymer of this present invention can be used in a photolithography employing the light of 157 nm because of excellent transmittance at 157 nm wavelength. In addition, from Examples 9 to 12, it is ascertained that the photoresist composition comprising the photoresist polymer according to the present invention has effective physical property as a photoresist.

As discussed earlier, a photoresist pattern having excellent durability, etching resistance, and developable property can be formed successfully by employing the photoresist composition of this present invention. And the photoresist composition of this present invention can be used in forming a minute pattern below 1 G DRAM as well as 4 G and 16 G Moreover, the photoresist polymer of this present invention has a low light absorbance at the 157 nm wavelength, and thus is suitable for a photolithography using VUV.

What is claimed is:

1. A photoresist monomer represented by following Formula 1:

Formula 1 wherein, l and m are individually integers ranging from 0 to 3:

$X_1$ and $X_2$ are individually selected from the group consisting of($C_1$–$C_{10}$) alkylene, O and S when l ranges from 1 to 3;

$X_1$ and $X_2$ are individually selected from the group consisting of ($C_2$–$C_{10}$) alkylene, O and S when l is O: and

$Y_1$, $Y_2$, $Y_3$, $Y_4$, $Y_5$, $Y_6$, $Y_7$ and $Y_8$ are individually selected from the group consisting of halogen, an alkyl partially substituted with halogen, and an alkyl completely substituted with halogen.

2. The photoresist monomer according to claim 1, wherein the $Y_1$, $Y_2$, $Y_3$, $Y_4$, $Y_5$, $Y_6$, $Y_7$ and $Y_8$ are individually selected from the group consisting of F, Cl, Br, I and $CF_3$.

3. The photoresist monomer according to claim 1, wherein the monomer of Formula 1 is selected from the group consisting of compounds of the Formulas 1b to 1d:

Formula 1b

Formula 1c

Formula 1d

4. A photoresist polymer comprising a repeating unit of the following Formula 4:

Formula 4 wherein, $R_1$, $R_2$ and $R_3$ are individually selected from the group consisting of H, halogen, $(C_1-C_{20})$ alkyl, (C1–C20) alkyl with halogen substituent(s), $(C_1-C_{20})$ alkyl containing an ether group (—O—), and $(C_1-C_{20})$ alkyl with halogen substituent(s) and containing an ether group;

$R_4$ is an acid labile protecting group;

$X_1$ and $X_2$ are individually selected from the group consisting of $(C_1-C_{10})$alkylene, O and S;

$Y_1$, $Y_2$, $Y_3$, $Y_4$, $Y_5$, $Y_6$, $Y_7$ and $Y_8$ are individually selected from the group consisting of halogen, an alkyl partially substituted with halogen, and an alkyl completely substituted with a halogen;

Z is O or S;

l and m are individually integers ranging from 0 to 3;

n is 0 or 1; and the ratio a:b:c falls within the ranges 0–60 mol %:5–80 mol %:0–90 mol %.

5. The photoresist polymer according to claim 4, wherein the $R_1$, $R_2$ and $R_3$ are individually selected from the group consisting of H, F, $(C_1-C_{20})$ alkyl, $(C_1-C_{20})$ perfluoroalkyl, $(C_1-C_{20})$ alkyl containing an ether group, $(C_1-C_{20})$ perfluoroalkyl containing an ether group, $(C_1-C_{20})$ alkyl partially substituted with F, and $(C_1-C_{20})$ alkyl partially substituted with F and containing an ether group.

6. The photoresist polymer according to claim 4, wherein the acid labile protecting group is selected from the group consisting of tert-butyl, tetrahydropyran-2-yl, 2-methyl tetrahydropyran-2-yl, tetrahydrofuran-2-yl, 2-methyl tetrahydrofuran-2-yl, 1-methoxypropyl, 1-methoxy-1-methylethyl, 1-ethoxypropyl, 1-ethoxy-1-methylethyl, 1-methoxyethyl, 1-ethoxyethyl, tert-butoxyethyl, 1-isobutoxyethyl and 2-acetylmenth-1-yl.

7. The photoresist polymer according to claim 4, wherein the repeating unit of the Formula 4 is selected from the group consisting of Formulas 4a to 4d:

8. A process of preparing a photoresist polymer comprising:
(a) admixing (i) a compound of Formula 7, and optionally (ii) at least one of the compound of Formula 5 and the compound of Formula 6; and
(b) adding a polymerization initiator into the resultant of step (a) to obtain a repeating unit of Formula 4:

Formula 7

-continued

Formula 4

Formula 5

Formula 6 wherein, $R_1$, $R_2$ and $R_3$ are individually selected from the group consisting of H, halogen, ($C_1$–$C_{20}$) alkyl, ($C_1$–$C_{20}$) alkyl with halogen substituent(s), ($C_1$–$C_{20}$) alkyl containing an ether group, and ($C_1$–$C_{20}$) alkyl with halogen substituent(s) and containing an ether group;

$R_4$ is an acid labile protecting group;

$X_1$ and $X_2$ are individually selected from the group consisting of ($C_1$–$C_{10}$)alkylene, O and S;

$Y_1$, $Y_2$, $Y_3$, $Y_4$, $Y_5$, $Y_6$, $Y_7$ and $Y_8$ are individually selected from the group consisting of halogen, an alkyl partially substituted with halogen and an alkyl completely substituted with a halogen;

Z is O or S;

l and m are individually integers ranging from 0 to 3;

n is 0 or 1; and the ratio a:b:c falls within the ranges 0–60 mol %:5–80 mol %:0–90 mol %.

9. The process according to claim 8, wherein the step (a) is carried out in a polymerization solvent selected from the group consisting of cyclohexanone, cyclopentanone, tetrahydrofuran, dimethylformamide, dimethylsulfoxide, dioxane, methylethylketone, benzene, toluene, xylene and mixtures thereof.

10. The process according to claim 8, wherein the polymerization initiator is selected from the group consisting of 2,2'-azobisisobutyronitrile(AIBN), benzoylperoxide, acetylperoxide, laurylperoxide, tert-butylperoxide and di-tert-butyl peroxide.

11. A photoresist composition comprising:
  (i) the photoresist polymer of claim 4;
  (ii) an organic solvent; and
  (iii) a photoacid generator.

12. The photoresist composition according to claim 11, wherein the photoacid generator is selected from the group consisting of phthalimidotrifluoromethane sulfonate, dinitrobenzyltosylate, n-decyl disulfone and naphthylimido trifluoromethane sulfonate.

13. The photoresist composition according to claim 12, wherein the photoacid generator further comprises a compound selected from the group consisting of diphenyl iodide hexafluorophosphate, diphenyl iodide hexafluoroarsenate, diphenyl iodide hexafluoroantimonate, diphenyl p-methoxyphenylsulfonium triflate, diphenyl p-toluenylsulfonium triflate, diphenyl p-isobutylphenylsulfonium triflate, diphenyl p-tert-butylphenylsulfonium triflate, triphenylsulfonium hexafluororphosphate, triphenylsulfonium hexafluoroarsenate, triphenylsulfonium hexafluoroantimonate, triphenylsulfonium triflate, dibutylnaphthylsulfonium triflate and mixtures thereof.

14. The photoresist composition according to claim 11, wherein the photoacid generator is present in an amount ranging from about 0.05 to about 10% by weight of the photoresist polymer.

15. The photoresist composition according to claim 11, wherein the organic solvent is selected from the group consisting of methyl 3-methoxypropionate, ethyl 3-ethoxypropionate, propylene glycol methyl ether acetate, cyclohexanone, 2-heptanone, ethyl lactate and mixtures thereof.

16. The photoresist composition according to claim 11, wherein the organic solvent is present in an amount ranging from about 500 to about 2000% by weight of the photoresist polymer.

17. A process for forming a photoresist pattern, comprising:
  (a) coating a photoresist composition of claim 11 on a substrate to form a photoresist film;
  (b) exposing the photoresist film to light; and
  (c) developing the exposed photoresist film to obtain a photoresist pattern.

18. The process according to claim 17, further comprising a soft baking step before step (b) and/or a post baking step after step (b).

19. The process according to claim 18, wherein the soft and post baking steps are individually performed at a temperature ranging from about 70 to about 200° C.

20. The process according to claim 17, wherein the sources of the light is selected from the group consisting of VUV, ArF, KrF, E-beam, EUV and ion beam.

21. The process according to claim 17, wherein the irradiation energy of the step (b) is in the range of from about 1 mJ/cm² to about 100 mJ/cm².

22. The process according to claim 17, wherein the step (c) is performed in alkaline developing solution.

23. A semiconductor element manufactured according to the process of claim 17.

* * * * *

UNITED STATES PATENT AND TRADEMARK OFFICE
CERTIFICATE OF CORRECTION

PATENT NO.    : 6,806,025 B2
DATED         : October 19, 2004
INVENTOR(S)   : Lee et al.

It is certified that error appears in the above-identified patent and that said Letters Patent is hereby corrected as shown below:

Column 12,
Line 27, after "when 1 is" please delete "O:" and insert -- O; -- in its place.

Column 13,
Line 24, please delete "(C1-C20)" and insert -- ($C_1$-$C_{20}$) -- in its place.

Signed and Sealed this

Third Day of May, 2005

JON W. DUDAS
*Director of the United States Patent and Trademark Office*